United States Patent
McMahon et al.

(10) Patent No.: US 10,365,343 B2
(45) Date of Patent: *Jul. 30, 2019

(54) MULTI-ECHO LENGTH AND OFFSET VARIED SATURATION (ME-LOVARS) METHOD FOR CHEMICAL EXCHANGE SATURATION TRANSFER (CEST) MR IMAGING

(71) Applicants: THE JOHNS HOPKINS UNIVERSITY, Baltimore, MD (US); KENNEDY KRIEGER INSTITUTE, INC., Baltimore, MD (US)

(72) Inventors: Michael T. McMahon, Columbia, MD (US); Xiaolei Song, Baltimore, MD (US); Jiadi Xu, Lutherville, MD (US)

(73) Assignees: The Johns Hopkins University, Baltimore, MD (US); Kennedy Krieger Institute, Inc., Baltimore, MD (US)

( * ) Notice: Subject to any disclaimer, the term of this patent is extended or adjusted under 35 U.S.C. 154(b) by 479 days.

This patent is subject to a terminal disclaimer.

(21) Appl. No.: 14/895,620

(22) PCT Filed: Jun. 3, 2014

(86) PCT No.: PCT/US2014/040599
§ 371 (c)(1),
(2) Date: Dec. 3, 2015

(87) PCT Pub. No.: WO2014/197419
PCT Pub. Date: Dec. 11, 2014

(65) Prior Publication Data
US 2016/0139228 A1 May 19, 2016

Related U.S. Application Data

(60) Provisional application No. 61/830,355, filed on Jun. 3, 2013.

(51) Int. Cl.
*G01V 3/00* (2006.01)
*G01R 33/561* (2006.01)
(Continued)

(52) U.S. Cl.
CPC ........ *G01R 33/5613* (2013.01); *A61B 5/0042* (2013.01); *A61B 5/055* (2013.01); *G01R 33/5601* (2013.01); *G01R 33/5605* (2013.01)

(58) Field of Classification Search
USPC ........................................................ 324/309
See application file for complete search history.

(56) References Cited

U.S. PATENT DOCUMENTS

| | | | |
|---|---|---|---|
| 2003/0042905 A1 | 3/2003 | Miyazaki et al. | |
| 2006/0109004 A1* | 5/2006 | Butts ................ | G01R 33/56563 324/307 |

(Continued)

*Primary Examiner* — Rodney E Fuller
(74) *Attorney, Agent, or Firm* — Johns Hopkins Technology Ventures

(57) ABSTRACT

A novel approach for CEST MR imaging is called Multi-echo Length and Offset VARied Saturation (Me-LOVARS) CEST. This method allows efficient collection of additional CEST data without penalty in scan time, which could be useful for enhancing the contrast, increasing the specificity or improving quantification of exchange. As CEST-MRI has shown promise at both the pre-clinical and clinical levels, including for detecting and grading brain tumors and evaluating ischemia, using either endogenous CEST contrast or through administration of CEST contrast agents. This fast and robust imaging method is suitable for accelerating image collection and widening the scope of applications for CEST-MRI.

14 Claims, 6 Drawing Sheets

(51) Int. Cl.
 *A61B 5/055* (2006.01)
 *A61B 5/00* (2006.01)
 *G01R 33/56* (2006.01)

(56) References Cited

U.S. PATENT DOCUMENTS

| | | |
|---|---|---|
| 2008/0319301 A1 | 12/2008 | Busse |
| 2010/0253340 A1 | 10/2010 | Corum et al. |
| 2012/0019245 A1 | 1/2012 | Reddy et al. |
| 2012/0271159 A1 | 10/2012 | Song et al. |
| 2013/0193966 A1* | 8/2013 | Larson ............... G01R 33/4608 324/309 |
| 2016/0187445 A1* | 6/2016 | McMahon ......... G01R 33/5605 600/420 |

* cited by examiner

MULTI-ECHO LENGTH AND OFFSET VARIED SATURATION (ME-LOVARS) METHOD FOR CHEMICAL EXCHANGE SATURATION TRANSFER (CEST) MR IMAGING

CROSS-REFERENCE TO RELATED APPLICATIONS

This application is a 35 U.S.C. § 371 U.S. national entry of International Application PCT/US2014/040599, having an international filing date of Jun. 3, 2014, which claims the benefit of U.S. Provisional Application No. 61/830,355, filed Jun. 3, 2013, the content of each of the aforementioned applications is herein incorporated by reference in their entirety.

GOVERNMENT SUPPORT

This invention was made with government support under R01 EB015031 and 1R01EB012590 awarded by the National Institutes of Health. The government has certain rights in the invention.

FIELD OF THE INVENTION

The present invention relates generally to medical imaging. More particularly the present invention relates to CEST magnetic resonance imaging.

BACKGROUND OF THE INVENTION

Chemical Exchange Saturation Transfer (CEST) imaging has been attracting attention due to its unique characteristics: 1) the ability to detect signals from low concentration species based on the highly selective saturation of rapidly exchanging spins and 2) the capability of detecting changes in environmental parameters in vivo including: pH, temperature and ion concentration. There have been a number of pre-clinical and now also clinical applications which involve either the detection of administered or endogenous CEST agents. A theme of many of these studies involves applying CEST imaging to cancer for characterization of tumor vasculature, metabolism, extracellular pH and nanocarrier uptake.

In order to detect CEST contrast, it is common practice to increment the frequency of a saturation pulse across a range of frequencies. The simple and most common method to detect and quantify CEST contrast is by calculating the asymmetry in the magnetization transfer ratio ($MTR_{asym}$) at the frequency of the exchangeable protons ($\Delta\omega$):

$$MTR_{asym} = \frac{(S(-\Delta\omega) - S(+\Delta\omega))}{S_0}$$

which is the subtraction of the two water signal intensities with saturation pulse at $+\Delta\omega$ and $-\Delta\omega$ with respect to water, $S(+\Delta\omega)$ and $S(-\Delta\omega)$, normalized by the signal without saturation ($S_0$), or by $S(-\Delta\omega)$ to amplify the dynamic range. Tumors and strokes display contrast on $MTR_{asym}$ maps at saturation offsets between 1-3.5 ppm from water, an effect that has been connected to the amide protons of extra soluble peptides/proteins found in brain tumors which resonate around 3.5 ppm from water, or changes in pH and has been termed Amide Proton Transfer (APT). The amount of APT signal produced by brain tumors was shown to correlate with histopathological grade in patients on clinical 3T scanners, and was also shown to be a marker that could differentiate tumor recurrence from radiation necrosis. There are also attempts to monitor tumor response to HIFU and chemotherapy.

Although CEST imaging has shown great potential for oncological imaging, there are obstacles towards widespread application, including the low Contrast-Noise-Ratio (CNR) of the images, sensitivity to field inhomogeneities, and susceptibility to interference from other sources of contrast. In addition, collection of CEST images can be quite time-consuming. A typical scheme for a CEST pulse sequence is shown in FIG. 1A. Before the water signal readout, a long frequency-selective continuous wave (CW) pulse or pulse train is applied at the resonance frequency of the agent to prepare the magnetization. The Saturation Preparation (Sat. Prep.) pulse(s) is usually on the order of seconds in order to obtain sufficient amplification of signal loss through multiple exchanges of saturated solute protons with water, i.e. low-concentration saturated solute protons are replaced by unsaturated water protons and the new protons are saturated. In addition, for most in vivo data the $MTR_{asym}$ value is not purely CEST contrast, but also includes interference from other sources of water signal loss generated by the saturation pulse, including conventional magnetization transfer contrast (MTC), direct saturation (DS) and relayed Nuclear Overhauser Effect (NOE) transfers. Finally, most endogenous CEST agents resonate between 1-4 ppm from water leading to low specificity for CEST measurements.

Because of the challenges mentioned above, new methods are needed which improve the specificity of CEST measurements or reduce image acquisition times. Recently several acquisition methods have been developed including methods to suppress MTC such as SAFARI, Two-frequency and VDMP and sequences for extracting components of exchange contrast e.g. CERT, Spin-Lock and FLEX. There are also sequences for accelerating CEST data acquisition, such as using RARE or FLASH, CEST-FISP, steady-state methods for fast 3D brain imaging of APT and recently methods based on gradients applied during saturation can push the speed of Z-spectrum collection to single-shot. Gradient-encoded offset methods are intriguing, but currently only have been demonstrated in vitro and might be very challenging in vivo due to inhomogeneous distribution of contrast.

One proposed strategy for improving CEST image specificity acquires multiple STw images with different saturation lengths ($t_{sat}$) to add another dimension of information describing the decay in the water signal. In simple phantoms (CEST agent in water/PBS), the changes in $MTR_{asym}$ as a function of saturation length ($t_{sat}$) can be used to measure exchange rates ($K_{sw}$), otherwise known as QUEST. In vivo, this Length and Offset VARied Saturation (LOVARS) data can be studied to separate tumor pixels from control brain tissue through the different $t_{sat}$-dependence of $MTR_{asym}$ values. This data can discriminate the different levels of interference from MTC, DS and NOE, through collecting $t_{sat}$-dependence information and increase CNR and the specificity of CEST imaging. Unfortunately, it is not practical to acquire images with multiple $t_{sat}$'s and also with multiple saturation offsets (Z-spectra) due to long scan times, although both of them are useful for improving the CEST imaging.

It would therefore be advantageous to provide an efficient and effective form of CEST magnetic resonance imaging, which enables multiple readouts of water signal during the

BRIEF DESCRIPTION OF THE FIGURES

FIG. 1A illustrates a graphical view of an acquisition scheme for a conventional CW CEST experiment. FIG. 1B illustrates a graphical view of an acquisition scheme for MeLOVARS, according to an embodiment of the present invention. FIG. 1C illustrates a graphical view of an Nth saturation preparation module in MeLOVARS highlighting the magnetizations for the different portions of the module.

FIG. 3A illustrates a graphical view of a Zspectra acquired only using ⅛ time of that for conventional method. FIG. 3B illustrates a graphical view of the QUESP data for SA(2) at different B1, and finally B1=3.6 uT is chosen for analyzing the ksw as in FIGS. 3C and 3D. FIG. 3C illustrates a graphical view of contrast build-up for glucose with different FA comparing with the conventional method. FIG. 3D illustrates a graphical view of contrast build-up for SA with different FA comparing with the conventional method. For compound 1, QUEST fittings: Ksw_Single=0.62, Ksw_FA10=0.63, Ksw_FA20=0.66, Ksw_FA30=0.52 (above 15% error). For compound 2, QUEST fittings: Ksw_Single=0.94, Ksw_FA10=0.98, Ksw_FA20=0.94, Ksw_FA30=1.80 (above 15% error).

FIG. 5A illustrates high-resolution MTw images. FIG. 5B illustrates conventional $MTR_{asym}$ maps with $T_{sat}$=0.5 s, 1 s, 1.5 s, 2 s and 2.5 s respectively, which requires 5×'s the scanner time.

FIG. 5C illustrates a CESTw image at $-\Delta\omega$ from the 5$^{th}$ Module readout in MeLOVARS scheme. FIG. 5D illustrates $MTR_{asym}$ maps for 5 MeLOVARS echoes respectively; Note that in both MeLOVARS echo1 in FIG. 5B and $T_{sat}$=0.5 s in FIG. 5D only the rim of the tumor is enhanced. FIG. 5E illustrates a principle component (PC) 2 map using PCA analysis of the 5 CESTw images at $-\Delta\omega$. FIG. 5F illustrates a PC2 map using PCA analysis of the 5 CESTw images at $+\Delta\omega$. FIG. 5G illustrates the $MTR_{asym}$ build-up for tumor core and for contralateral control region, $\Delta MTR_{asym}$ were obtained by taking the subtraction of $MTR_{asym}$ for Tumor core and $MTR_{asym}$ for the contralateral WM. FIG. 5H illustrates the Average MTRasym changes for tumor and for contralateral tissue is different. FIG. 5I illustrates an ADC map of the diffusion-weighted image. FIG. 5K illustrates H&E staining for one frozen slice of mouse 1 showing the tumor region. FIGS. 5J and 5L illustrate MeLOVARS maps with B1=1 uT and B1=3 uT, noted that the color bar scale changes, where the $MTR_{asym}$ value is higher for B1=3 uT and lower for B1=1 uT.

SUMMARY

Figure 1A:
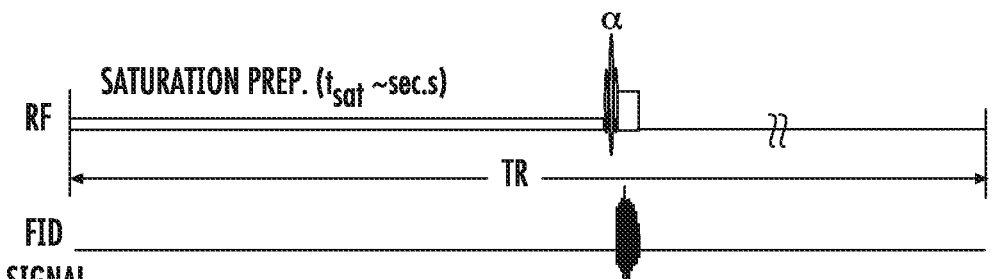
FIGS. 1A-1C illustrate graphical views of image acquisition schemes.

The foregoing needs are met, to a great extent, by the present invention, wherein in one aspect a method for magnetic resonance imaging of a subject includes generating a magnetization using an magnetic resonance imaging machine. The method includes applying "N" number of iterative modules to achieve multiple readouts. The "N" number of iterative modules each include a saturation preparation component, a readout component, and a flip back component. The method also includes processing the multiple readouts into an image of the subject.

In accordance with an aspect of the present invention, the method includes using N equals approximately 3 to 8 modules and using modules with a length of $t_{sat}$/N. Alternately, the method includes using modules with a length of approximately 0.3 to 1 second. The method includes using the readout component comprising a low flip angle fast gradient echo readout sequence. The method also includes using a flip angle of $\alpha$ and using a flip back pulse for retaining the magnetization. The method includes defining magnetization as longitudinal magnetization $$M_N^{z,sat} = x_s \varepsilon k_{sw} T_{1,w} \cdot M_N^z \cdot e^{-\frac{T_{sat}}{N \cdot T_{1,w}}} = b \cdot M_N^z \cdot e^{-\frac{T_{sat}}{N \cdot T_{1,w}}}$$

in the absence of saturated protons. The method includes defining magnetization as longitudinal and transverse magnetization and defining magnetization as $$M_N^{z,\alpha} = M_N^{z,sat} \cdot \cos\alpha \qquad \text{a)}$$

$$M_N^{x,\alpha} = M_N^{z,sat} \cdot \sin\alpha \qquad \text{b)}$$

when applying the flip angle component. Additionally, the method includes defining longitudinal magnetization after the Nth module as $$M_N^{z,\alpha} = M_N^{z,\alpha} \cdot \cos\alpha + M_N^{x,\alpha} \cdot e^{-\frac{TE}{T2}} \cdot \sin\alpha$$
$$= b \cdot M_N^z \cdot e^{-\frac{T_{sat}}{N \cdot T_{1,w}}} \left[ 1 - \sin^2\alpha \left( 1 - e^{-\frac{TE}{T2}} \right) \right].$$

The method also includes defining an iterative relationship between modules as $$M_N^{z,\alpha} = b \cdot M_{N-1}^{z,\alpha} \cdot e^{-\frac{T_{sat}}{N \cdot T_{1,w}}} \left[ 1 - \sin^2\alpha \left( 1 - e^{-\frac{TE}{T2}} \right) \right]$$

-continued $$= b \cdot M_{N-2}^{z,-\alpha} \cdot e^{-\frac{2T_{sat}}{N \cdot T_{1,w}}} \left[1 - \sin^2\alpha\left(1 - e^{-\frac{TE}{T_2^*}}\right)\right]^2$$

...  ...

$$= b \cdot M_0^{z,-\alpha} \cdot e^{-\frac{T_{sat}}{T_{1,w}}} \left[1 - \sin^2\alpha\left(1 - e^{-\frac{TE}{T_2^*}}\right)\right]^N.$$

The method includes using a $T_2$ decay term. The method can also be executed using a non-transitory computer readable medium.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention provides a novel approach for CEST MR imaging, called Multi-echo Length and Offset VARied Saturation (Me-LOVARS) CEST. This method allows efficient collection of additional CEST data without penalty in scan time, which could be useful for enhancing the contrast, increasing the specificity or improving quantification of exchange. As CEST-MRI has shown promise at both the pre-clinical and clinical levels, including for detecting and grading brain tumors and evaluating ischemia, using either endogenous CEST contrast or through administration of CEST contrast agents. This fast and robust imaging method is suitable for accelerating image collection and widening the scope of applications for CEST-MRI.

Further, the present invention includes a hybrid CW-pulsed approach, Multi-echo LOVARS (Me-LOVARS), using fast T1 mapping for collecting multiple images at varied saturation lengths within each TR. This can be used either for correcting contrast maps against MTC, B0, B1 inhomogeneity or for further contrast characterization such as to determine $K_{ex}$. Method Images were acquired on SCID/NCR mice (n=4) bearing intracranial xenografts derived from human glioblastoma neurospheres (HSR-GBM1A) on a Bruker Biospec 11.7T scanner, with a 72 mm birdcage resonator as transmitter and a surface array coil as receiver. MR parameters were: 3 sat. pulses with $T_{sat}$=0.8 s, B1=2 uT, 4 segment EPI with 7.85 ms each, flip angle ($\alpha$)=25o, TR/TE=5 s/5.27 ms, FOV=16.5×15.5×1 mm. and matrix size=96×64.

Figure 1B:
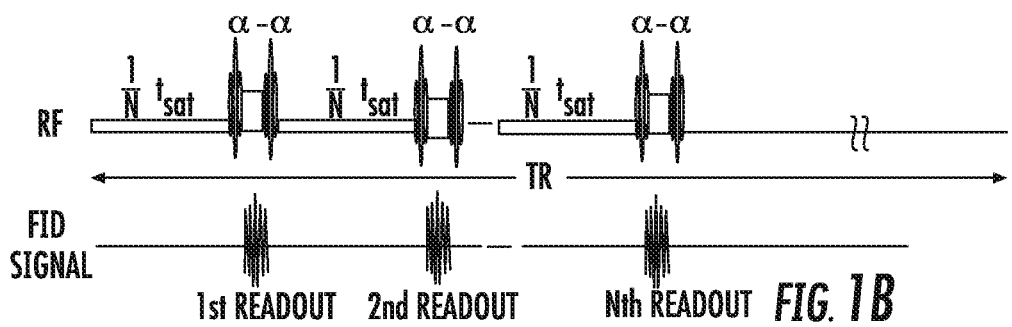
Figure 1C:
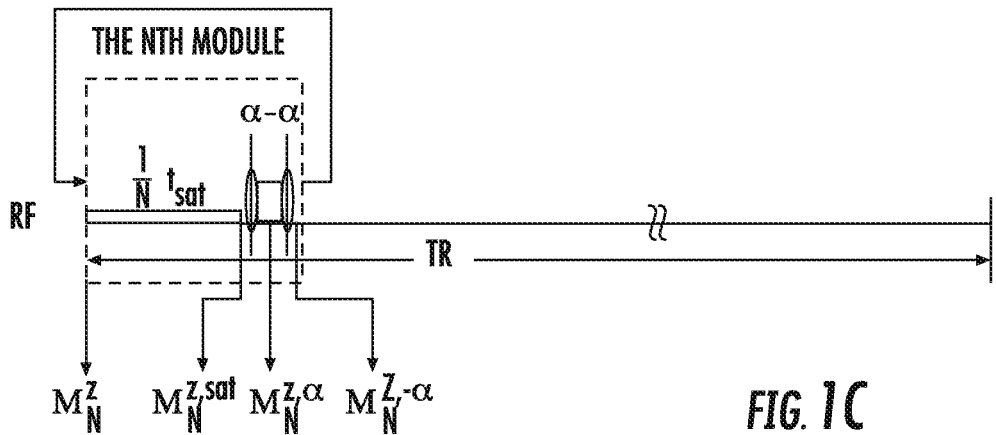
Figure 2A:
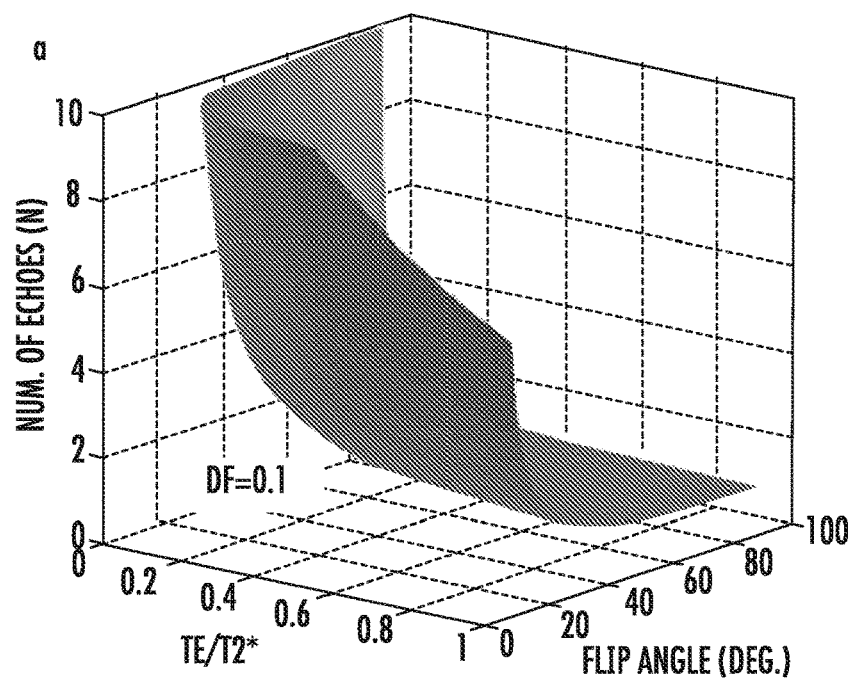
FIG. 2A illustrates a graphical view of a Contour surface for the Nth FID signal readout in MeLOVARS $M_N^{x,\alpha}$ (MeLOVARS) with a Decay Factor (DF)=10% comparing to the signal using conventional single readout method $M_N^{x,\alpha}$ (Conv.) as a guidance for choosing measurement parameters: Num. of Modules, TE/T2* and Flip Angle.
Figure 2B:
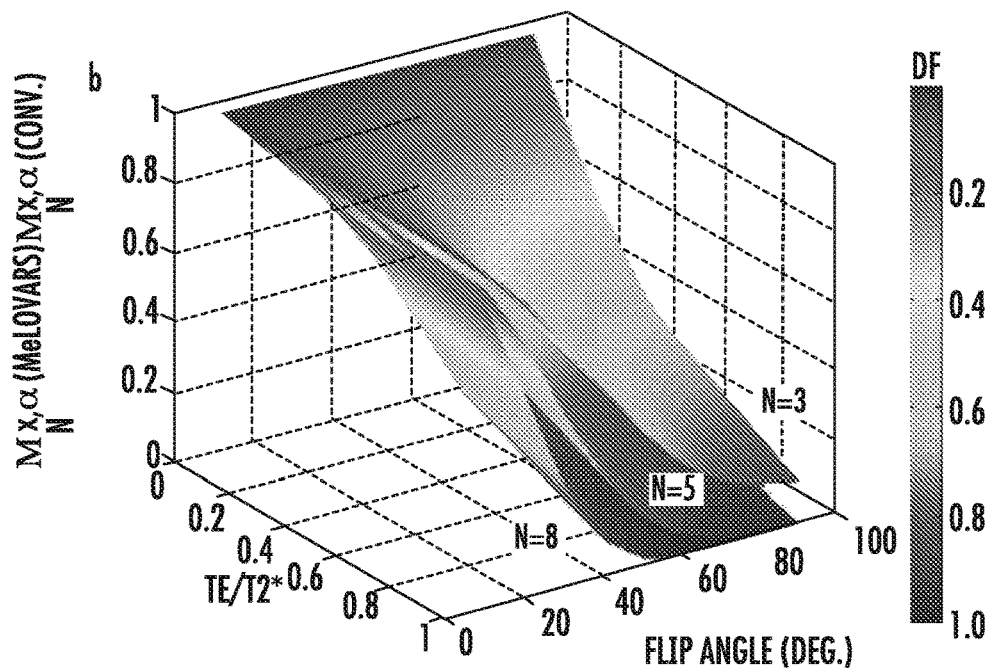
FIG. 2B illustrates a graphical view of Simulations of DF and $M_N^{x,\alpha}$(MeLOVARS)/$M_N^{x,\alpha}$(Conv.) as a function of TE/T2*, $\alpha$ with N equal to 3, 5, 8, which were used in the phantom and in vivo experiments.

An imaging sequence in accordance with the present invention provides that the long saturation pulse is divided into 3-5 blocks of 0.5 s-1 s(n×$T_{sat}$, n=1, . . . , 5), in front of low flip-angle fast gradient echo read-outs (here EPI) with a flip-back pulse after the image readout to retain the longitudinal magnetization. FIGS. 1A-1C illustrate first, second, and third gradient echo readouts according to the present invention. As a result, multiple $T_{sat}$ readouts are obtained within one TR, i.e. without penalty in experiment time, In other words, using the same scan time as conventional methods which only read images after the entire saturation process, the ME-LOVARS method acquires 3-5 APTw images with varied saturation lengths (FIGS. 2A and 2B). The B0-corrected APT maps (MTRasym at 3.5 ppm) of the 3 sat lengths show comparable contrast values to the conventional RARE-readout. The 3 Z-spectra allow the observation of MTC, APT, and NOE build-up. Although there are more artifacts in the normal brain region in an EPI-based MTRasym map than those from the RARE map, by taking an average of the 3 maps, tumor contrast values increased by 2-3%. The number of echoes and $\alpha$ need to be optimized for different applications.

Instead of employing a single long Sat. Prep. module of length $t_{sat}$ (i.e. >1 sec.) before echo readouts, the Me-LOVARS method divides this Sat. Prep. into N=3-8 sub-modules, each with a length of $t_{sat}$/N (~0.3 sec.-1 sec.), and in between inserts a low flip-angle (FA=$\alpha$) fast gradient echo read-out sequence (here EPI), followed by a flip back pulse (FA=$-\alpha$) for retaining longitudinal magnetization (FIG. 1B). Thus, multiple readouts are achieved during the Sat. Prep. To understand the signal changes caused by the multiple readouts, the Me-LOVARS method is displayed (FIG. 1C) as N iterative modules containing a Sat. Prep. part, a readout part and a flip-back part.

Supposing the longitudinal magnetization before the Nth MeLOVARS Module is $M_N^z$, based on a simplified two-pool exchange model including a small solute pool and large water pool, the longitudinal magnetization in the absence of back exchange of saturated protons becomes:

$$M_N^{z,sat} = x_s \varepsilon k_{sw} T_{1,w} \cdot M_N^z \cdot e^{-\frac{T_{sat}}{N \cdot T_{1,w}}} = b \cdot M_N^z \cdot e^{-\frac{T_{sat}}{N \cdot T_{1,w}}} \quad [1]$$

$$\text{where } x_s = \frac{[\text{exchangable protons}]}{[H_2O]},$$

the fractional concentration of solute protons, $\varepsilon$ is the saturation efficiency, and $k_{sw}$ is the forward solute proton to water exchange rate.

When applying a small flip angle pulse, the longitudinal and transverse magnitizations becomes:

$$M_N^{z,\alpha} = M_N^{z,sat} \cdot \cos\alpha \quad \text{a)}$$

$$M_N^{x,\alpha} = M_N^{z,sat} \cdot \sin\alpha \quad \text{b) [2]}$$

Where $M_N^{x,\alpha}$ is the Nth FID signal prior to readout for reconstructing the Nth STw images. After a short Gradient-Echo based readout, the transverse magnetization decays to $$M_N^{x,\alpha} \cdot e^{-\frac{TE}{T_2^*}}.$$

Upon application of a flip-back pulse, FA=$-\alpha$, the longitudinal magnetization after the Nth module is:

$$M_N^{z,-\alpha} = M_N^{z,\alpha} \cdot \cos\alpha + M_N^{x,\alpha} \cdot e^{-\frac{TE}{T_2^*}} \cdot \sin\alpha \quad [3]$$

-continued $$= b \cdot M_N^z \cdot e^{-\frac{T_{sat}}{N \cdot T_{1,w}}} \left[1 - \sin^2\alpha\left(1 - e^{-\frac{TE}{T_2^*}}\right)\right]$$

As the starting magnetization of the Nth module ($M_N^z$) is equal to that at the end of the (N−1)th module $M_{N-1}^{z,-\alpha}$, an iterative relationship between the successive modules can be achieved:

$$M_N^{z,-\alpha} = b \cdot M_{N-1}^{z,-\alpha} \cdot e^{-\frac{T_{sat}}{N \cdot T_{1,w}}} \left[1 - \sin^2\alpha\left(1 - e^{-\frac{TE}{T_2^*}}\right)\right] \quad [4]$$

$$= b \cdot M_{N-2}^{z,-\alpha} \cdot e^{-\frac{2T_{sat}}{N \cdot T_{1,w}}} \left[1 - \sin^2\alpha\left(1 - e^{-\frac{TE}{T_2^*}}\right)\right]^2$$

$$\ldots \ldots$$

$$= b \cdot M_0^{z,-\alpha} \cdot e^{-\frac{T_{sat}}{T_{1,w}}} \left[1 - \sin^2\alpha\left(1 - e^{-\frac{TE}{T_2^*}}\right)\right]^N$$

Combining Eq.4 and Eq.2b, the Nth FID signal readout $M_N^{x,\alpha}$ is given by:

$$M_N^{x,\alpha} = b \cdot M_{N-1}^{z,-\alpha} \cdot e^{-\frac{T_{sat}}{N \cdot T_{1,w}}} \cdot \sin\alpha \quad [5]$$

$$= b \cdot M_0^z \cdot e^{-\frac{T_{sat}}{T_{1,w}}} \cdot \sin\alpha \cdot \left[1 - \sin^2\alpha\left(1 - e^{-\frac{TE}{T_2^*}}\right)\right]^{N-1}$$

Compared to the conventional signal-readout sequence with the same FA:

$$M^{x,\alpha}(conv.) = b \cdot M_0^z \cdot e^{-\frac{T_{sat}}{T_{1,w}}} \cdot \sin\alpha \quad [6]$$

the Nth module readout of Me-LOVARS has an extra T2*-weighted Decay Factor $$(DF) = 1 - \left[1 - \sin^2\alpha\left(1 - e^{-\frac{TE}{T_2^*}}\right)\right]^{N-1},$$

which is also a function of the measurement parameters including: N, $\alpha$, and TE, as well as the local $T_2^*$.

EXAMPLES

Exemplary implementations of the present invention are described herein, in order to further illustrate the present invention. The exemplary implementations are included merely as an example and is not meant to be considered limiting. Any implementation of the present invention on any suitable subject known to or conceivable by one of skill in the art could also be used, and is considered within the scope of this application.

To evaluate the MeLOVARS sequence, a phantom was prepared consisting of four 5 mm NMR tubes, with one filled with 0.01 M phosphate-buffered saline (PBS) as the negative control, and the other three each filled with a CEST agent at a concentration of 25 mM in PBS. The three agents were: 1) D-Glucose (Δω=0.9-1.5 ppm, pH 7.4); 2) Salicylic Acid (Δω=9.3 ppm, pH 7.1); 3) 5-Chloro-2-(methyl-sulfo-namido)benzoic acid (Δω=7.2 ppm, pH 7.1) with all agents titrated using NaOH and HCl.

All in vitro MR scans were acquired on a Bruker vertical 750 MHz scanner at a temperature of 310K. A 2-shot EPI readout scheme was used with TR/TE=8 sec.s/5.25 ms, EPI module time=7.05 ms and Matrix Size=32×32. Z-spectra were acquired using a CW saturation pulse with $B_1$=2.4, 3.6, and 4.8 μT and the saturation offset incremented 0.3 ppm for −9.9 ppm→−6.9 ppm, −2.7 ppm→2.7 ppm, and 6.9 ppm→9.9 ppm and 0.6 ppm increment for −6.9→−2.7 ppm and 2.7 ppm→6.9 ppm.

Simulations

To simulate the CEST contrast produced by the MeLOVARS sequence for mice bearing glioblastomas and optimize $\alpha$ and N, the 4-pool bloch equations were numerically solved with the semi-solid pool, the amide pool, the aliphatic pool and the water pool with Δω=0 ppm, 3.6 ppm, −3.6 ppm and 0 ppm respectively. Each module of MeLOVARS was simulated as the pulse-sequence described in FIG. 1C, including a Sat. pulse, an excitation pulse of flip angle $\alpha$ and a $T_2$ decay term. Based on an initial guess of parameter values and range reported previously, the 5 experimental MeLOVARS Z-spectra for both the tumor area and control normal white matter (WM) are fit to the model to further determining the relaxation parameters, pool sizes and exchange rates for the 3 pools other than water, using the Levenberg-Marquardt optimization algorithm, With the fitted parameters in Table 1, the 5 $MTR_{asym}$ values measured through MeLOVARS change was simulated as a function of for both tumor and contralateral tissue, to optimize the N and a for the in vivo experiments.

TABLE 1

Fitting parameters derived from the WM of healthy mice used in the 4-pool simulations

|  | 'Free water' | | 'amide protons' | | 'semi-solid protons' | | 'aliphatic protons' | |
| --- | --- | --- | --- | --- | --- | --- | --- | --- |
|  | Tumor | WM | Tumor | WM | Tumor | WM | Tumor | WM |
| $T_1$ (ms) | 2100 | 1900 | 2100 | 1900 | 2100 | 1900 | 2100 | 1900 |
| $T_2$ (ms) | 47 | 25 | 15 | | 0.0092 | | 0.95 | |
| Pool size(M) | 111 | | 0.58 | 0.28 | 4.2 | 8.5 | 0.99 | 2.8 |
| Δω (ppm) | 0 | | 3.6 | | 0 | | −3.6 | |
| Exchange rate($s^{-1}$) | — | | 25 | | 69 | | 13 | |

In Vivo Animal Studies

MR images were acquired on SCID/NCR mice (n=4) bearing intracranial xenografts derived from human glioblastoma neurospheres (HSR-GBM1A) on a Bruker Biospec 11.7T scanner, using a 72 mm body coil for transmission and a 4-channel phase-array surface coil for reception. Two sets of MR parameters were used for testing Me-LOVARS (N=3 or 5): N=3 saturation pulse length=0.8 sec.($\frac{1}{3}T_{sat}$), 4 segment EPI (7.85 ms per segment), $\alpha$=25°, saturation offsets= [±4.8, ±4.2, ±3.9, ±3.6, ±3.3, ±3, ±2.4, ±1.5, ±0.6, ±0.3, 0] ppm or N=5 saturation pulse length=0.5 sec.($\frac{1}{5}T_{sat}$), 6 segment EPI (6.4 ms per segment), $\alpha$=25°, TR/TE=4 s/4.3 ms, FOV=16.5×15.8×1 mm, matrix size=96×64. $B_1$ was set to 1.2 uT, 2 uT and 3 uT. Conventional CEST images were also acquired using a single 6 segment EPI readout ($t_{sat}$=2.4 sec) using the same parameters as MeLOVARS. For MeLOVARS, the Z-spectra acquisition time is 8 min 48 sec, plus an additional 80 sec for the WASSR image-set for B0 mapping and corrections, resulting in ~10 min of scanning.

Post-Processing

All data were processed using custom-written MATLAB scripts. For both phantom and in vivo study, a voxel-by-voxel Z-spectra $B_0$ correction was performed through interpolating the original data to every 0.1 ppm using a piecewise polynomial fitting, with $B_0$ values from WASSR. CEST contrast was quantified by $MTR_{asym}=(S(-\Delta\omega)-S(+\Delta\omega)/S_0$, $S_0$ is the image with same FA readout without saturation pulse. For glucose with faster exchange ($k_{sw}$>1 k Hz) and with three $\Delta\omega$'s, calculated an average $MTR_{asym}$ of [0.9 ppm, 1.2 ppm, 1.5 ppm], similar to the previous studies. For other agents with a single $\Delta\omega$, $MTR_{asym}$ is only calculated at the peak CEST frequency. To increase the CNR for in vivo mice study, the contrast maps for amide (—NH, APT weighted) and amine (—NH$_2$) freq. were obtained by averaging $MTR_{asym}$ from 3.3 to 3.9 ppm, and from 2.6 to 3 ppm, respectively.

Except for the conventional $MTR_{asym}$ analysis, Principal Component Analysis (PCA) was also applied in processing the STw images of different $T_{sat}$ at +$\Delta\omega$ or -$\Delta\omega$ acquired by MeLOAVRS, namely the time-resolved CEST data. As a data-driven multivariate statistic technique, PCA had been used in analyzing the time series data in PET, fMRI, dynamic contrast enhanced (DCE) MRI and optical imaging. And here it is used to extract the independent variations (named Principal Components) among images with multiple $T_{sat}$'s, supposing one of the biggest variances is due to the build-up of CEST contrast (for the +$\Delta\omega$ dataset) or the NOE contrast (for the -$\Delta\omega$ dataset).

Results

Simulations

Signal readout of the Nth module in MeLOVARS can be simply estimated by multiplying the conventional single-readout signal with the same length with an extra $T_2^*$-weighted term $$\left[1-\sin^2\alpha\left(1-e^{-\frac{TE}{T_2^*}}\right)\right]^{N-1},$$

which is a function of the measurement parameters number of modules (N), FA ($\alpha$) and TE.

FIG. 2A displays a contour surface plot based on Eqs. [5] and [6] with DF=10% which can be used to select the appropriate $\alpha$ and N based on the $T_2^*$ over the volume of interest and the TE's attainable on the scanner. As is shown, with a small FA and TE/$T_2^*$, Me-LOVARS produces very similar readout signals (i.e. even for the Nth images, DF<10%) as produced through the conventional CW saturation method, but with 1/N of the scan time. FIG. 2B plotted the DF and $M_N^{x,\alpha}$(MeLOVARS)/$M_N^{x,\alpha}$(Conv.) as a function of TE/$T_2^*$ and $\alpha$, with N=8, 5 and 3, which was used in the phantoms and in vivo experiments. As seen, to ensure DF of the Nth readout <10% with $\alpha$=20, TE/$T_2^*$<0.14 is required for N=8, TE/$T_2^*$<0.25 for N=5, TE/$T_2^*$<0.59 for N=3.

Figures 3A, 3B, 3C, 3D:
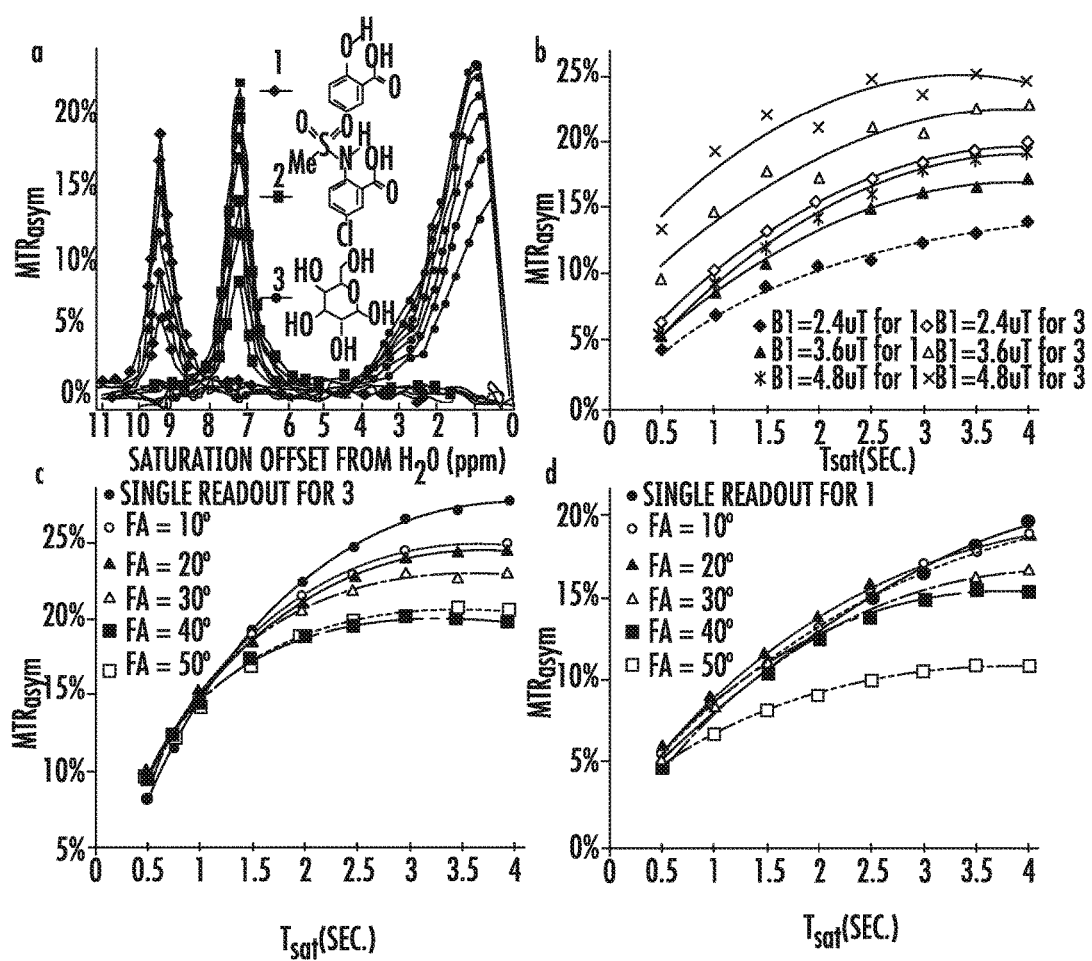
FIGS. 3A-3D illustrate graphical views of phantom experiment results for 3 CEST agents with different $\Delta\omega$ and exchange rates.

FIGS. 3A-3D illustrate graphical views of phantom experiment results for 3 CEST agents with different $\Delta\omega$ and exchange rates. FIG. 3A illustrates a graphical view of a Zspectra acquired only using $\frac{1}{8}$ time of that for conventional method. FIG. 3B illustrates a graphical view of the QUESP data for SA(2) at different B1, and finally B1=3.6 uT is chosen for analyzing the ksw as in FIGS. 3C and 3D. FIG. 3C illustrates a graphical view of contrast build-up for glucose with different FA comparing with the conventional method. FIG. 3D illustrates a graphical view of contrast build-up for SA with different FA comparing with the conventional method. For compound 1, QUEST fittings: Ksw_Single=0.62, Ksw_FA10=0.63, Ksw_FA20=0.66, Ksw_FA30=0.52 (above 15% error). For compound 2, QUEST fittings: Ksw_Single=0.94, Ksw_FA10=0.98, Ksw_FA20=0.94, Ksw_FA30=1.80 (above 15% error).

Phantom Experiments

A phantom study based on the simulations described above was also performed to determine whether the MeLOVARS acquisition scheme enables more rapid quantification of exchange rates ($K_{sw}$) using the QUEST method, and how the data compares with those collected using a single module. Z-spectra were collected with num. of modules N=8 (from 0.5 s to 4 s with every 0.5 s increment) to fit using numerical simulations, allowing 8× acceleration over the conventional 8 single readouts. FIG. 3A shows the build-up of $MTR_{asym}$ curves as increasing $T_{sat}$'s for three representative agents and the negative control PBS. MeLOVARS also works robustly for different saturation power, as in FIG. 3B three sets of QUEST data for SA and Glucose were plotted. Note that $MTR_{asym}$ for glucose increases more from B1=1.2 uT to 3.6 uT than that for SA due to the faster exchange. Further the MeLOVARS build-up curves were compared with $\alpha$ varied from 10 deg to 50 deg to the conventional method ($\alpha$=20 deg). For SA, when the $\alpha$<30 deg the QUEST curves are almost identical to that using the conventional method (FIG. 3D). Whereas for glucose, even for $\alpha$=10 deg and 20 deg, there is a drop of $MTR_{asym}$ when N>3, presumably due to the shorter $T_2^*$ and the interference with direct water saturation. For compound 1, the results of QUEST fittings are, $K_{sw\_single}$=0.62, $K_{sw\_\alpha=10\ deg}$=0.63, $K_{sw\_\alpha=20\ deg}$=0.66, $K_{sw\_\alpha=30\ deg}$=0.52 (above 15% error). For compound 2, QUEST fittings are: $K_{sw\_single}$=0.94, $K_{sw\_\alpha=10\ deg}$=0.98, $K_{sw\_\alpha=20\ deg}$=0.94, $K_{sw\_\alpha=30\ deg}$=1.80 (above 15% error). It's reasonable that there is a big error for $\alpha\geq30$ deg, as indicated by Eq. [5] and FIGS. 2A and 2B, for $\alpha$=20 deg, TE/$T_2^*$<0.14 (i.e. $T_2^*$>50 ms) could be easily achieved to ensure DF<10%, whereas for $\alpha$=30 deg, DF<10% requires TE/$T_2^*$<0.06, i.e. $T_2^*$>120 ms which is difficult to guarantee due to the ultra-high $B_0$ field (17.5 Tesla) and the field inhomogeneities.

In Vivo Imaging of Mice Brain

MeLOVARS data was also acquired on mice brain bearing glioblastoma, with number of module=5 and each of 0.5 sec. in length, which produces multiple Z-spectra (FIGS. 4A-4D) and $MTR_{asym}$ spectra and maps (FIGS. 5A-L) in 8.5 min.

Figures 4A, 4B, 4C, 4D:
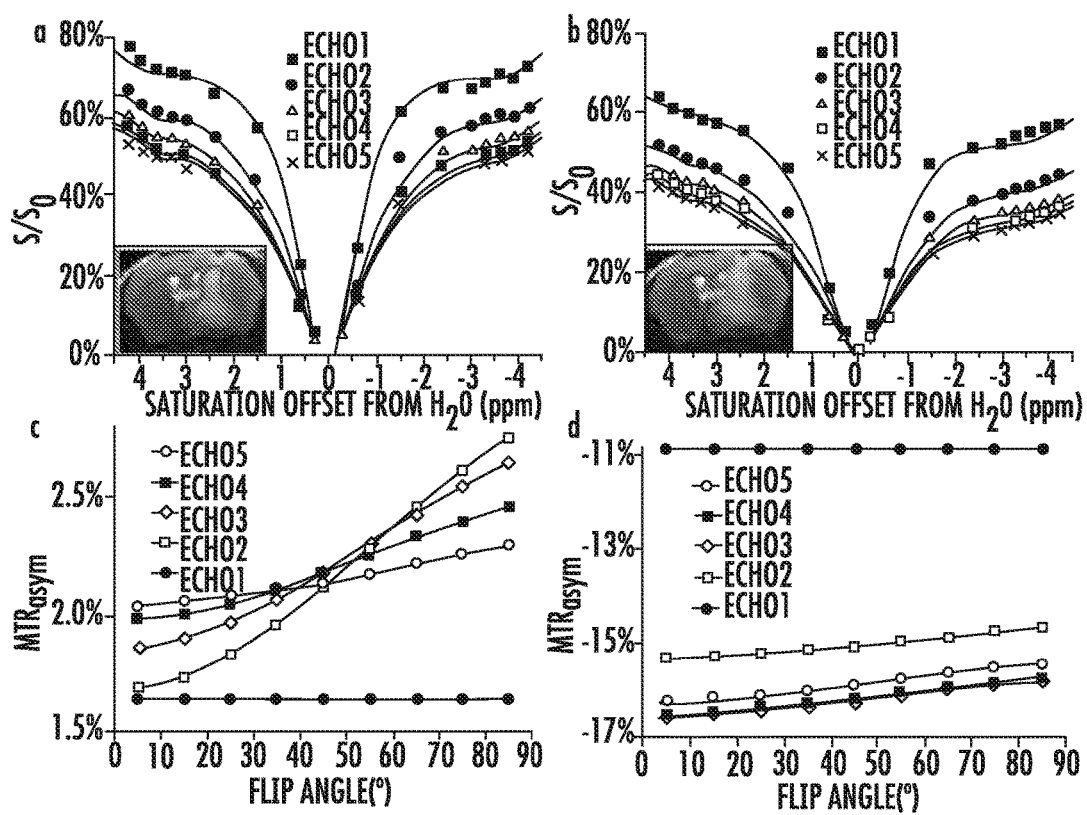
FIG. 4A illustrates a graphical view of in vivo 4-pool Bloch-fitting of tumor tissue.
FIG. 4B illustrates a graphical view of in vivo 4-pool Bloch-fitting of a control experiment of normal white matter tissue.
FIG. 4C illustrates a graphical view of MTRasym changes as a function of FA for the tumor tissue of FIG. 4A.
FIG. 4D illustrates a graphical view of MTRasym changes as a function of FA for the normal white matter tissue of FIG. 4B.

As is known, for in vivo CEST imaging, multiple pools are saturated which exchange with $H_2O$, thus the actual measured $MTR_{asym}$ is a combination of CEST, MT, DS and also the NOE from the aliphatic protons with frequency at the other side of water, where the simplified 2-pool model may not be applicable. Using a 4-pool Bloch model, the experimental 5 Z-spectra from MeLOVARS for both tumor (FIG. 4A) and the contralateral WM (FIG. 4B) were fitted with the fitted parameters listed in Table 1. Then multiple $MTR_{asym}$ (N=5) changes as a function of flip angle (α) were simulated for both tumor and the control WM. FIG. 4C shows that for tumor area with longer water $T_2$, bigger APT pool and smaller MT and NOE pools, the actual $MTR_{asym}$ value increases from Module1 to Module5 when α<35 deg, but stops with α>35 deg. Note that since the normalization using signals with same α, Module1 doesn't change as α. However, for the WM with bigger MT and NOE contribution, as well as shorter $T_2$, the $MTR_{asym}$ values are biggest for Module1 and are more than 5% lower for the following Modules. FIG. 4A illustrates a graphical view of in vivo 4-pool Bloch-fitting of tumor tissue. FIG. 4B illustrates a graphical view of in vivo 4-pool Bloch-fitting of a control experiment of normal white matter tissue. FIG. 4C illustrates a graphical view of MTRasym changes as a function of FA for the tumor tissue of FIG. 4A. FIG. 4D illustrates a graphical view of MTRasym changes as a function of FA for the normal white matter tissue of FIG. 4B.

Figures 5A, 5B, 5C, 5D, 5E, 5F, 5G, 5H, 5I, 5J, 5K, 5L:
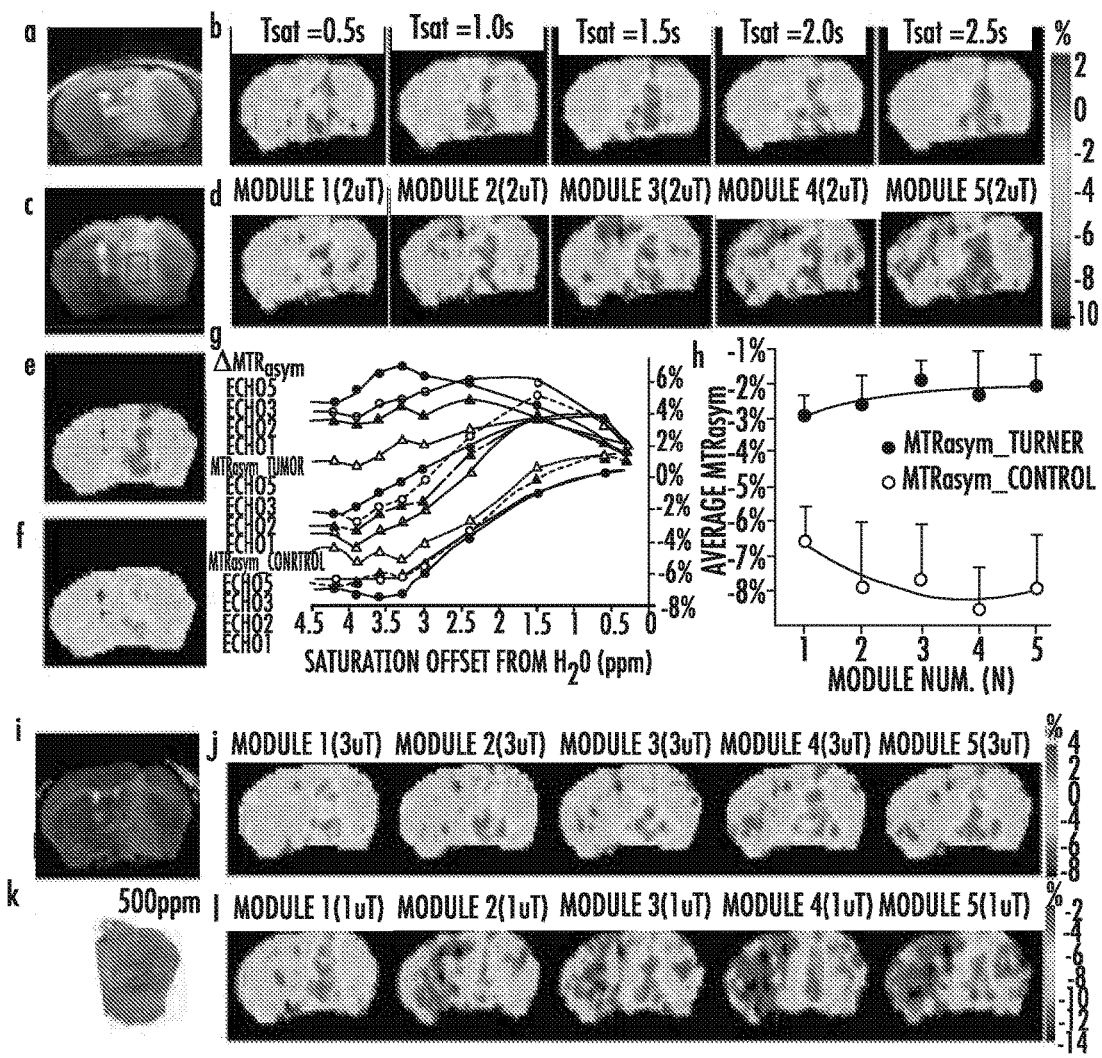
FIGS. 5A-5L illustrate MeLOVARS performance in mice bearing glioblastomas.

As an illustration, FIGS. 5A-5L show the performance of MeLOVARS with number of module N=5 and each of 0.5 sec. in length, compared with the conventional method. A high-resolution (128×96) MTw image is shown in FIG. 5A, and FIG. 5B shows five lower-resolution (96×64) $MTR_{asym}$ maps which were acquired using the conventional method (Conv.), with $T_{sat}$=0.5 s, 1 s, 1.5 s, 2 s and 2.5 s respectively. FIG. 5C shows the CESTw image at +3.6 ppm from the 5$^{th}$ Module readout using MeLOVARS with saturation power of 2 uT, and the $MTR_{asym}$ maps for 5 module readouts (FIG. 5D), respectively, which only used ⅕ of that for FIG. 5B. Note that for both $T_{sat}$=0.5 s in b) and MeLOVARS Module1 in d only the rim of tumor are enhanced, which could be missed if only one pre-determined $T_{sat}$ is used. The 5 STw images of MeLOVARS with different $T_{sat}$ could also be analyzed using PCA, where FIG. 5E) is the map of 2$^{nd}$ Principal Component (PC2) from the five images at −Δω, which is correlated with the build-up of NOE and MT contrast as $T_{sat}$ increases. Similarly FIG. 5F) is PC2 map from the five images at +Δt, which is correlated with the build-up of CEST and MT contrast as $T_{sat}$ increases. MeLOVARS enables acquisition of 5 $MTR_{asym}$ curves simultaneously, with FIG. 5G) showing the build-up of $MTR_{asym}$ contrast for the tumor core ($MTR_{asym}$_Tumor), the contralateral control region ($MTR_{asym}$_Ctrl) and $\Delta MTR_{asym}$ which were obtained by taking the subtraction of $MTR_{asym}$ for tumor core and $MTR_{asym}$ for the contralateral WM. FIG. 5H) further plotted the average value of $MTR_{asym}$_tumor and $MTR_{asym}$_ctrl for all the 3 mice imaged, which $MTR_{asym}$_tumor keep increasing from N=1 to N=5 and $MTR_{asym}$_ctrl is decreasing; Other than saturation-based contrast, tumor can also be enhanced in the ADC map of the diffusion-weighted image (FIG. 5I)), which is further confirmed by H&E staining for one frozen slice of the mouse brain showing the tumor region (FIG. 5K)). MeLOVARS is also working robustly with different saturation power $B_1$=1 uT and $B_1$=3 uT, with the $MTR_{asym}$ maps shown in FIGS. 5J&5L. Noted that the color bar scale changes, where the MTRasym value is higher for $B_1$=3 uT and lower for $B_1$=1 uT.

The $MTR_{asym}$ contrast values and the CNR of images were quantitatively compared using the conventional method (Conv.) and MeLOVARS (Me.) for this group of mice (n=3), as shown in Table 2. The first 3 rows compare the averaged $MTR_{asym}$_Tumor, $MTR_{asym}$_Ctrl and $\Delta MTR_{asym}$ of the three mice and their standard deviation, for the cony. method with $T_{sat}$=0.5 s, 1 s, 1.5 s, 2 s and 2.5 s and MeLOVARS with Module 1 to Module 5, respectively. As seen, the averaged values of $MTR_{asym}$_ Tumor are very similar for each column of Conv. and Me, while Me. got lower $MTR_{asym}$_Ctrl values than those using the Conv. with the same saturation length, which is presumably due to the extra $T_2^*$-weighted decay term, $[1-\sin^2 \alpha(1-e^{TE/T_2*})]^{N-1}$ for the Nth Me-LOVARS readout, which could be pronounced at 11.7 T. As a result, $\Delta MTR_{asym}$ in MeLOVARS is increasing from 3.6% for N=1 to −6% for N=4&5, comparing to the values keeping in between 3.6% to 4.5% using the conventional methods. The decreased $MTR_{asym}$ contrast in the contralateral side could also be observed in FIGS. 5A-5L, when comparing the maps in FIG. 5B with FIG. 5D, FIG. 5K, and FIG. 5L.

For the Nth module readout in MeLOVARS (or the conventional method with the same corresponding $T_{sat}$), CNR was calculated by expanding it using $$CNR = M_N^{x,\alpha} - \Delta\omega - M_N^{x,\alpha} + \Delta\omega - M_N^{x,\alpha} - \Delta\omega - M_N^{x,\alpha} +$$
$$\Delta\omega = M_{0,N}^{x,\alpha} \cdot M_{0,N}^{x,\alpha} \sigma - \Delta\omega 2 + \sigma +$$
$$\Delta\omega 2 = MTR_{asym} \cdot SNR_{0,N}\sqrt{2}$$

where $MTR_{asym} = [M_N^{x,\alpha}(+\Delta\omega) - M_N^{x,\alpha}(-\Delta\omega)]/M_{0,N}^{x,\alpha}$ and $SNR_{0,N}$ is the Signal-Noise-Ratio for the Nth module without saturation. Thus, supposing there is no changes in the noise level σ, compared to conventional one, the SNR $S_0$ of the Nth module will drop a factor of $$\left[1 - \sin^2\alpha\left(1 - e^{-\frac{TE}{T_2}}\right)\right]^{N-1}, \text{ as } M_{0,N}^{x,\alpha} = M^{x,\alpha}(conv.) \cdot DF,$$

as shows the decreasing SNR of Me. from N=1 to N=5 in the 4$^{th}$ row in Table2. However, as the contrast between tumor and control tissue, $\Delta MTR_{asym}$, is slightly higher for MeLOVARS when N>1, the resulting CNR of MeLOVARS is also higher than that of Conv. method with the same $T_{sat}$ when N>1.

FIGS. 6A-6D show another example of MeLOVARS with 3 Module readouts with sat. length of 0.8 s for 2 mice (FIGS. 6B, 6C, and 6D), in comparison with the single readout of conventional CEST (FIGS. 6A and 6C), which further proved the efficiency and robustness of MeLOVARS. As is seen, the 3rd ST-weighted images using MeLOVARS (right image of FIG. 6B) is almost identical to that produced by the conventional method using the same EPI parameters (FIG. 6A), indicating the similar image quality of the MeLOVARS readouts that are right following the ST sub-module, same as the conventional one. However, the $MTR_{asym}$ build-up around 3.5 ppm is not very obvious (FIG. 6C), probably due to interfering the NOE effects and the exponential build-up manner. Except for the APT contrast, the three MeLOVARS contrast maps from amine protons were around 2.4 ppm, which also shows the different contrast maps for the Module1 and Module 2&3. As mentioned before, for all the three FA, ⅓ $T_{sat}$ with saturation transfer was not build-up steadily, while the contrast of ⅔ $T_{sat}$ and $T_{sat}$ is pretty good. In addition, the image quality can be further improved by average the three. There is also another indication of build-up curves. In addition, when adding up all the N readout, the CNR could consider increasing >√N times of the conventional method with the same α, as also shown in Table 2.

The present invention is directed to a MeLOVARS method proposed for acquisitions of images with multiple saturation length ($t_{sat}$) without extra time cost, which is readily applied to both phantom and in vivo CEST imaging. A simple analytical guideline of how to choose Number of Modules (N), Flip Angle ($\alpha$) and TE/T2*, to ensure a small Decay Factor (e.g. DF<10%) compared to the conventional methods with a single module, which is caused by the dephasing processes of the multiple readouts is proposed. For the phantom, 3 CEST agents were used with varying offsets from 0.9 ppm to 9.3 ppm, demonstrating that MeLO-VARS could enable fast QUEST acquisition and accurate fitting of $K_{sw}$ when $\alpha$<30 deg. at a high field strength ($B_0$=17.6 Tesla). When $\alpha$>=30, the MeLOVARS contrast start dropping for the larger N's compared to the conventional one with same $T_{sat}$, this is presumably because the local small T2* at this ultra-high field. For example, according to the parameter guidance of Eq. [5] and FIG. 2, DF<10% requires TE/$T_2$*<0.06 (i.e. $T_2$*>120 ms), which is difficult to guarantee at field strength of 17.6 Tesla because of the reduced $T_2$, increased susceptibility effect and field inhomogeneities.

Figure 6:
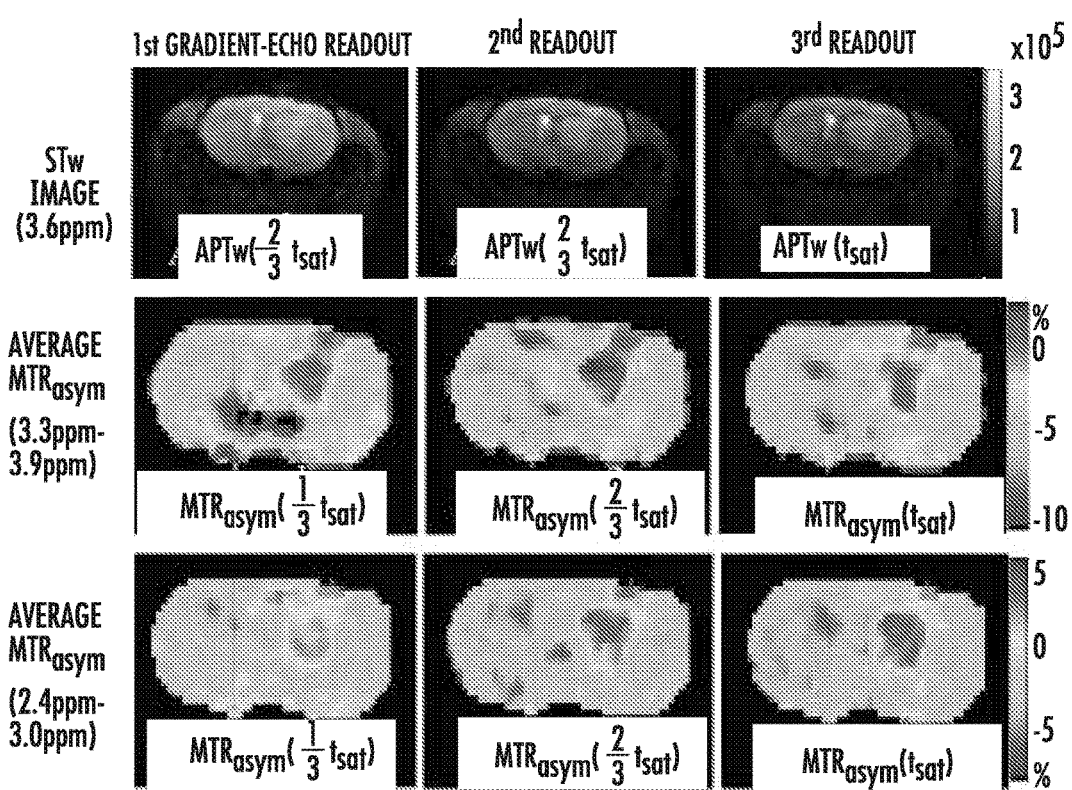
FIG. 6 illustrates images showing the flexibility of the method, according to an embodiment of the present invention.

One big advantage of MeLOVARS is that, it could be readily implemented to in vivo CEST imaging sequences based on gradient-echo readouts (GE or GRE) that have been used at both high field scanners and low field ones. As a proof MeLOVARS for imaging the endogenous APT contrast was applied in mice bearing glioblastoma at a filed strength of 11.7 Tesla, which could generate multiple Z-spectra, MTRasym Spectra and contrast maps with different effective Tsat's. As shown in FIGS. 5&6 and also quantitatively in Table 2, each module of MeLOVARS has either higher or comparable ΔMTRasym and the corresponding CNR than that by the conventional method with same readout sequence and parameters (i.e. GE-EPI). The N-fold image-yield could lead to an increasing of CNR by $\sqrt{N}$. The N groups of experimental Zspectra with different Tsat values were fit to a 4-pool Block equation model, where the fitting of multi-pool parameters become more stable as a result of the N-times more measured points. In addition to the frequently-used $MTR_{asym}$ analysis, and also processed the 5 STw images of different $T_{sat}$ at +Δω side and −Δω side separately using the data-driven multivariate statistic technique, PCA, which could completely avoid the interference between CEST (e.g. APT, AMEX) and NOE. As the same time of denoising using all the 5 images, PCA extracts the independent variations (named Principal Components) among images with multiple $T_{sat}$'s, supposing one of the biggest variances is due to the build-up of CEST contrast (for the +Δω dataset) or the NOE contrast (for the −Δω dataset). There could be several methods for analyzing MeLOVARS data, such as previous LOVARS and a radiometric method of images with different $T_{sat}$ to cancel out effects from relaxation and RF spill-over effects.

It should be noted that the methods described herein can be executed with a program(s) fixed on one or more non-transitory computer readable medium. The non-transitory computer readable medium can be loaded onto a computing device, server, imaging device processor, smartphone, tablet, phablet, or any other suitable device known to or conceivable by one of skill in the art. It should also be noted that herein the steps of the method described can be carried out using a computer, non-transitory computer readable medium, or alternately a computing device, microprocessor, or other computer type device independent of or incorporated with an imaging or signal collection device. The computing device can be integrated with the imaging device for collecting data or can be networked by wire or wirelessly with the imaging device. Indeed, any suitable method of calculation known to or conceivable by one of skill in the art could be used. It should also be noted that while specific equations are detailed herein, variations on these equations can also be derived, and this application includes any such equation known to or conceivable by one of skill in the art. A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape.

Researchers have also started to investigate the amount of APT contrast produced by other types of tumors including: lung, breast, and prostate cancer. Regarding to the gradient-echo based readout used in MeLOVARS, there could be concerns practically, especially at high field or for body applications. For example, MeLOVARS was validated for in vivo imaging of mice bearing glioblastoma at 11.7 Tesla. And the contrast heterogeneity at the control tissue may appear on the Me-LOVARS maps with N>1 (FIG. 5B), which is presumably caused by the shorter and heterogeneous T2* at high $B_0$ field due to the imperfect shimming, the air-tissue interface and the distribution of magnetic susceptibility. Fortunately at clinical low-field scanners (e.g. 1.5 Tesla and 3 Tesla) with longer and more homogeneous T2*, gradient-echo readout sequences are used very frequently esp. in brain such as in fast T1w imaging, Dynamic Contrast Enhanced (DCE) imaging, perfusion and BOLD functional imaging. For example, T2* values of mice brain gray matter could be varied between 7-28 ms at 11.7 Tesla, compared to ~50 ms of human frontal gray matter at 3 Tesla. Thus, as indicated by FIG. 2 and Eq.[5], the more than twice longer T2* allows using a higher N and a at 3 Tesla. i.e, N could reach 10 if same $\alpha$ and TE are used. Another advantage of Gradient-echo readout is that, the smaller excitation flip angle results in less disturbance from magnetic equilibrium and therefore shorter relaxation recovery times. (e.g. used a TR=4 s compared with in spin echo TR>=5 s). Thus, although the small a sacrifice the signal in the transverse plane, the reduced scan time will increase the efficiency. As CNR and its normalization as scan time of CEST-EPI was discussed previously as a function of TR and $\alpha$, thus the Me-LOVARS could be estimated by multiply a DF term (Eq. [5]) accordingly. Actually the decay factor can also be estimated using Eq.[5], as in FIG. 6A and b, for N=3, $\alpha$=25 deg and the average T2* is considered as 20 ms, DF is only ~5%. In addition, the total CNR could be increased up to $\sqrt{N}$ times, simply by averaging the N readouts.

The proposed a CEST acquisition method, named Multi-Echo Length and Offset VARied Saturation (Me-LOVARS) rapidly acquires multiple STw images of different effective $T_{sat}$, without extra scan time.

For phantoms MeLOVARS collects images with 8 $t_{sat}$'s from 0.5 s to 4 s simultaneously, enabling the measurement of the exchange rates for three CEST agents. For in vivo imaging of mice brain bearing glioblastomas, MeLOVARS enable acquisition of 5 Z-spectra, $MTR_{asym}$ spectra and contrast maps in 8.5 min, with 5 $t_{sat}$'s from 0.5 s to 2.5 s, where in each module the $MTR_{asym}$ difference between tumor and control tissue and the corresponding Contrast-Noise-Ratio (CNR) was shown either higher or comparable than those by conventional method. The MeLOVARS data could be used for fitting the multi-pool exchange model, separating CEST and NOE by analyzing the contrast buildup and improving CNR $\sqrt{N}$ times via image averaging.

In addition, although the present invention has only focused on the endogeneous APT contrast of brain tumor in the manuscript, this method is applicable to many applications either using the endogenous molecules glutamate, creatine, and glycosaminoglycans, or the exogenous compounds.

TABLE 2

MTRasym Contrast and CNR comparison for Conv. And MeLOVARS at 11.7 Tesla

| (n = 3) | | $T_{sat}$ = 0.5 s (Module1) | $T_{sat}$ = 1 s (Module2) | $T_{sat}$ = 1.5 s (Module3) | $T_{sat}$ = 2 s (Module4) | $T_{sat}$ = 2.5 s (Module5) |
|---|---|---|---|---|---|---|
| $MTR_{asym}$_Tumor (%) | Conv. | −0.9 ± 0.3 | −1.8 ± 1.0 | −1.4 ± 0.4 | −2.0 ± 0.7 | −2.1 ± 0.5 |
| | Me. | −2.4 ± 0.6 | −2.2 ± 0.9 | −1.4 ± 0.6 | −1.8 ± 1.2 | −1.6 ± 0.9 |
| $MTR_{asym}$_Ctrl. (%) | Conv. | −4.9 ± 0.2 | −6.0 ± 1.2 | −6.0 ± 1.0 | −5.9 ± 1.1 | −5.8 ± 0.6 |
| | Me. | −6.0 ± 0.9 | −7.4 ± 1.8 | −7.2 ± 1.6 | −8.1 ± 1.2 | −7.4 ± 1.5 |
| $\Delta MTR_{asym}$ (%) | Conv. | 4.0 ± 0.1 | 4.2 ± 0.2 | 4.5 ± 0.6 | 3.9 ± 0.5 | 3.6 ± 0.0 |
| | Me. | 3.6 ± 0.8 | 5.2 ± 1.6 | 5.8 ± 1.5 | 6.2 ± 1.2 | 5.9 ± 1.8 |
| SNR_$S_0$ | Conv. | 74 ± 2.5 | 74 ± 2.5 | 74 ± 2.5 | 74 ± 2.5 | 74 ± 2.5 |
| | Me. | 81 ± 0.8 | 68 ± 3.6 | 60 ± 4.6 | 51 ± 4.3 | 56 ± 2.9 |
| CNR_$\Delta MTR_{asym}$ | Conv. | 3.6 ± 0.2 | 3.7 ± 0.0 | 4.1 ± 0.4 | 3.5 ± 0.3 | 3.3 ± 0.1 |
| | Me. | 3.6 ± 0.8 | 4.4 ± 1.5 | 4.3 ± 1.5 | 3.9 ± 0.7 | 4.1 ± 1.5 |

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. A method for magnetic resonance imaging of a subject comprising:
   generating a magnetization using an magnetic resonance imaging machine;
   applying "N" number of iterative modules to achieve multiple readouts;
   wherein the "N" number of iterative modules each comprise a saturation preparation component, a readout component, and a flip back component;
   processing the multiple readouts into an image of the subject.

2. The method of claim 1 further comprising using N equals approximately 3 to 8 modules.

3. The method of claim 1 further comprising using modules with a length of $t_{sat}$/N.

4. The method of claim 1 further comprising using modules with a length of approximately 0.3 seconds to 1 second.

5. The method of claim 1 further comprising using the readout component comprising a low flip angle fast gradient echo readout sequence.

6. The method of claim 5 further comprising using a flip angle of $\alpha$.

7. The method of claim 1 further comprising using a flip back pulse for retaining the magnetization.

8. The method of claim 1 further comprising defining magnetization as longitudinal magnetization:

$$M_N^{z,sat} = x_s \varepsilon k_{sw} T_{1,w} \cdot M_N^z \cdot e^{-\frac{T_{sat}}{N \cdot T_{1,w}}} = b \cdot M_N^z \cdot e^{-\frac{T_{sat}}{N \cdot T_{1,w}}}$$

in the absence of saturated protons.

9. The method of claim 8 further comprising defining longitudinal magnetization after the Nth module as $$M_N^{z,-\alpha} = M_N^{z,\alpha} \cdot \cos\alpha + M_N^{x,\alpha} \cdot e^{-\frac{TE}{T_2}} \cdot \sin\alpha$$
$$= b \cdot M_N^z \cdot e^{-\frac{T_{sat}}{N \cdot T_{1,w}}} \left[1 - \sin^2\alpha \left(1 - e^{-\frac{TE}{T_2}}\right)\right].$$

10. The method of claim 1 further comprising defining magnetization as longitudinal and transverse magnetization.

11. The method of claim 1 further comprising defining magnetization as $$M_N^{z,\alpha} = M_N^{z,sat} \cdot \cos\alpha \qquad \text{a)}$$

$$M_N^{x,\alpha} = M_N^{z,sat} \cdot \sin\alpha \qquad \text{b)}$$

when applying the flip angle component.

12. The method of claim 1 further comprising defining an iterative relationship between modules as $$M_N^{z,-\alpha} = b \cdot M_{N-1}^{z,-\alpha} \cdot e^{-\frac{T_{sat}}{N \cdot T_{1,w}}} \left[1 - \sin^2\alpha \left(1 - e^{-\frac{TE}{T_2}}\right)\right]$$
$$= b \cdot M_{N-2}^{z,-\alpha} \cdot e^{-\frac{2T_{sat}}{N \cdot T_{1,w}}} \left[1 - \sin^2\alpha \left(1 - e^{-\frac{TE}{T_2}}\right)\right]^2$$
$$\dots \dots$$
$$= b \cdot M_0^{z,-\alpha} \cdot e^{-\frac{T_{sat}}{T_{1,w}}} \left[1 - \sin^2\alpha \left(1 - e^{-\frac{TE}{T_2}}\right)\right]^N.$$

13. The method of claim 1 further comprising using a $T_2$ decay term.

14. The method of claim 1 further comprising executing the method using a non-transitory computer readable medium.

* * * * *